United States Patent [19]

Okuda et al.

[11] Patent Number: 5,168,918

[45] Date of Patent: Dec. 8, 1992

[54] CASTING OF DENTAL METALS

[75] Inventors: Reiichi Okuda, Sendai; Norio Kojima, Ichikawa; Kenichi Iiyama, Tokyo; Yoshinobu Yamamura, Kawasaki; Yasutaro Ito; Shohei Hayashi, both of Tokyo, all of Japan

[73] Assignee: GC Corporation, Tokyo, Japan

[21] Appl. No.: 697,619

[22] Filed: May 9, 1991

[30] Foreign Application Priority Data

May 18, 1990 [JP] Japan ................................. 2-126963

[51] Int. Cl.$^5$ .............................................. B22D 27/02
[52] U.S. Cl. ...................................... 164/495; 164/514
[58] Field of Search ................. 164/494, 495, 512, 514

[56] References Cited

U.S. PATENT DOCUMENTS 3,977,462  8/1976  Ohara .
4,254,817  3/1981  Kidowaki et al. ................... 164/514

FOREIGN PATENT DOCUMENTS 0018450  11/1980  European Pat. Off. .
63-273563  11/1988  Japan ................................. 164/495

Primary Examiner—Kuang Y. Lin
Attorney, Agent, or Firm—Oblon, Spivak, McClelland, Maier & Neustadt

[57] ABSTRACT

A method for casting dental metals with a casting apparatus including a hermetically sealed casting chamber in which an arc electrode is located above, a crucible made of an electrically conductive material is positioned below the arc electrode, and a mold provided with a closed vent is disposed below the crucible, the method including by positioning a dental metal ingot on the crucible, evacuating the casting chamber to vacuum, feeding a small amount of an inert gas at such a pressure as to induce arc discharge all over the upper surface of the ingot, thereby melting the ingot placed on the crucible by arc discharge from the arc electrode, pouring the thus obtained molten metal into a mold through its inlet, and immediately feeding an additional amount of the inert gas into the casting chamber to increase its internal pressure to a level suitable for casting. Also the additional amount of the inert gas is rapidly fed into the casting chamber through a gas tank in the vicinity of the casting chamber.

2 Claims, 3 Drawing Sheets

CASTING OF DENTAL METALS

BACKGROUND OF THE INVENTION

1. Field of the Invention

The present invention relates to a method for casting such dental metals as titanium designed to make plate frames, clasps, etc. in the dental technical field, which enables high-quality products with neither casting deficiencies nor casting cavities to be cast be melting dental metal ingots by arc discharge.

2. Statement of the Prior Art

In the dental technical field, titanium has been used for CAST plate, clasps, etc., because it is light in weight, has a certain strength and excels in corrosion resistance and bioaffinity.

So far, metal frames, etc. used for, e.g. crowns or porcelain-fused-to-metal crowns have been cast by melting dental metals with the use of suitable techniques such as high-frequency melting and pouring the molten metals in molds, because the dental metals are noble metals relatively difficult to oxidize. Since the above-mentioned titanium has the property of being likely to undergo oxidization, it should be melted in an atmosphere of such an inert gas as argon. To meet such demand, reliance has been placed on a casting technique wherein dental metal ingots are melted by arc discharge and the obtained molten metals are poured in molds.

According to this casting technique, an arc electrode is disposed above in a hermetically sealed melting chamber, and a crucible made of an electrically conductive material is positioned just below the arc electrode. With the arc electrode and the crucible connected to a cathode and an anode, respectively, the dental metal ingot to be cast is first placed on the crucible. After evacuation to vacuum, the melting chamber is then filled with such an inert gas as argon until its internal pressure amounts to a pressure nearly equal to atmospheric pressure. Subsequently, the ingot is melted by arcs occurring from the arc electrode. Finally, the molten metal is poured into a mold chamber through the inlet of a mold located in said mold chamber which is partitioned from said melting chamber by a partition wall provided with a through-hole formed in its portion positioned below said crucible.

When titanium is used with this casting technique, it should be rapidly poured into the mold through its inlet, partly because the melting point of titanium is higher than melting points of common dental metals, and partly because titanium has to be cast with the mold maintained at room temperature as it cools down and solidifys rapidly—due to the fact that it reacts with mold material at such a high temperature as to cast common noble metal alloys. In other words, titanium must be poured under pressure into the mold by increasing pressure of the melting chamber to make a pressure difference between the melting chamber and the mold chamber.

The mold used is constructed from investment materials composed of a binder/aggregate combination. More specifically, the binder and aggregate are kneaded together with water or an exclusive liquid into slurry. After that, a wax model is invested in the slurry and cured at room temperature, followed by burning out wax at about 700° C. in furnace.

Owing to some air permeability available with such investment material, such investment material may be used for casting noble metal alloys forming part of metal frames, etc. used with crowns or porcelain-fused-to-metal crowns. This is because if it is pressurized with a pressure difference made between the melting and mold chambers, then an increase in the in-mold gas pressure is so suppressed due to its air permeability that the molten dental metal can be well poured into the mold.

Among common investment materials, however, there is a gypsum-bonded investment material using gypsum as the binder. At 700° C. or higher, this material increases in air permeability and decreases in heat resistance, since gypsum decomposes thermally at that temperature and so cannot retain its crystal form. For instance, when a high temperature dental metal like titanium is cast with that investment material, it react with each other to evolve gases in an amount which is so large that the gases cannot escape only through the inherent air permeability the investment material has. This would cause an increase in the pressure in the casting region of the mold, making it impossible to pour the predetermined amount of the molten dental metal in the mold. Othewise gases would be entrained in the molten metal, giving rise to cavities. In order to cast a high temperature dental metal, use has thus been made of a phosphate-bonded investment material using a phosphate as a binder. With this phosphate type of a material in which the binder phosphate combines with a metal oxide to form an amorphous product, gas emissions are limited even upon heated at high temperatures, since it undergoes no or little change in state and is of increased heat resistance. However, this leads to another defect that its air permeability is badly limited. For that reason, it has been proposed to use coarse aggregates for increased air permeability, thereby reducing a pressure rise in the casting regions of molds when molten dental metal are poured in them. However, this method makes the surfaces of casting products rough but, nonetheless, fails to obtain sufficient air permeability.

Thus, when no sufficient air permeability is obtained, the internal pressure of the casting region in the mold is too increased to pour the predetermined amount of molten dental metal into the mold. This gives rise to such disadvantages as casting deficiencies and entrainment of gases in the metal melt, resulting in casting cavities.

Arc melting of a dental metal ingot at around atmospheric pressure causes arcs to concentrate on their local points under the influences of magnetic blow, etc., often making its uniform melting impossible and thereby causing the dental metal ingot to be locally heated to high temperatures. While the molten dental metal ingot in its entirety, the molten metal reacts with the crucible material. In order to prevent this, additional special mechanisms for moving the electrodes are needed.

In order to solve the above-mentioned defects of the prior art, the present invention seeks to provide a method for casting dental metals which can produce well-smoothened castings by stable arc melting with no fear of causing casting deficiencies or cavities.

SUMMARY OF THE INVENTION

We have made strenuous studies to achieve the above-mentioned object and so have invented a method for casting dental metals with a casting apparatus including a hermetically sealed casting chamber in which an arc electrode is located above, a crucible made of an electrically conductive material is positioned below said arc electrode, and a mold provided with a closed vent is disposed below said crucible, said method being characterized by positioning a dental metal ingot on said crucible, evacuating said casting chamber to vacuum, feeding a small amount of an inert gas at such a pressure as to induce arc discharge all over the upper surface of said ingot, thereby melting said ingot placed on said crucible by arc discharge from said arc electrode, pouring the thus obtained molten metal into a mold through its inlet, and immediately feeding an additional amount of the inert gas into the said casting chamber to increase its internal pressure to a level suitable for casting.

According to this invention, uniform arc melting of dental metal ingots is achievable, since local arc discharge can be prevented by keeping low the pressure of the internal gas in the casting chamber in which they are positioned.

According to this invention, the defect of casting deficiencies and cavities are caused by a fact that the inner pressure of the mold increased when the molten dental metal is poured into the inlet of the mode, since it is difficult to impart sufficient air permeability to the investment material. Such defect- or cavity-free castings can be obtained by keeping the internal pressure of the casting chamber low until dental metal ingots are melted and poured into a mold through its inlet, and feeding an additional amount of the inert gas into the casting chamber immediately following the pouring of the molten metal into the mold through its inlet.

According to a preferable embodiment of this invention wherein the additional amount of the inert gas is rapidly supplied into the casting chamber through a gas tank positioned in the vicinity of the casting chamber, it is possible to obtain castings of even higher quality. This is never achieved with common inert gas cylinders which cannot supply large volumes at a time.

BRIEF DESCRIPTION OF THE DRAWINGS

The present invention will now be explained, by way of example alone, with reference to the accompanying drawings in which.

DETAILED EXPLANATION OF THE INVENTION

Figure 1:
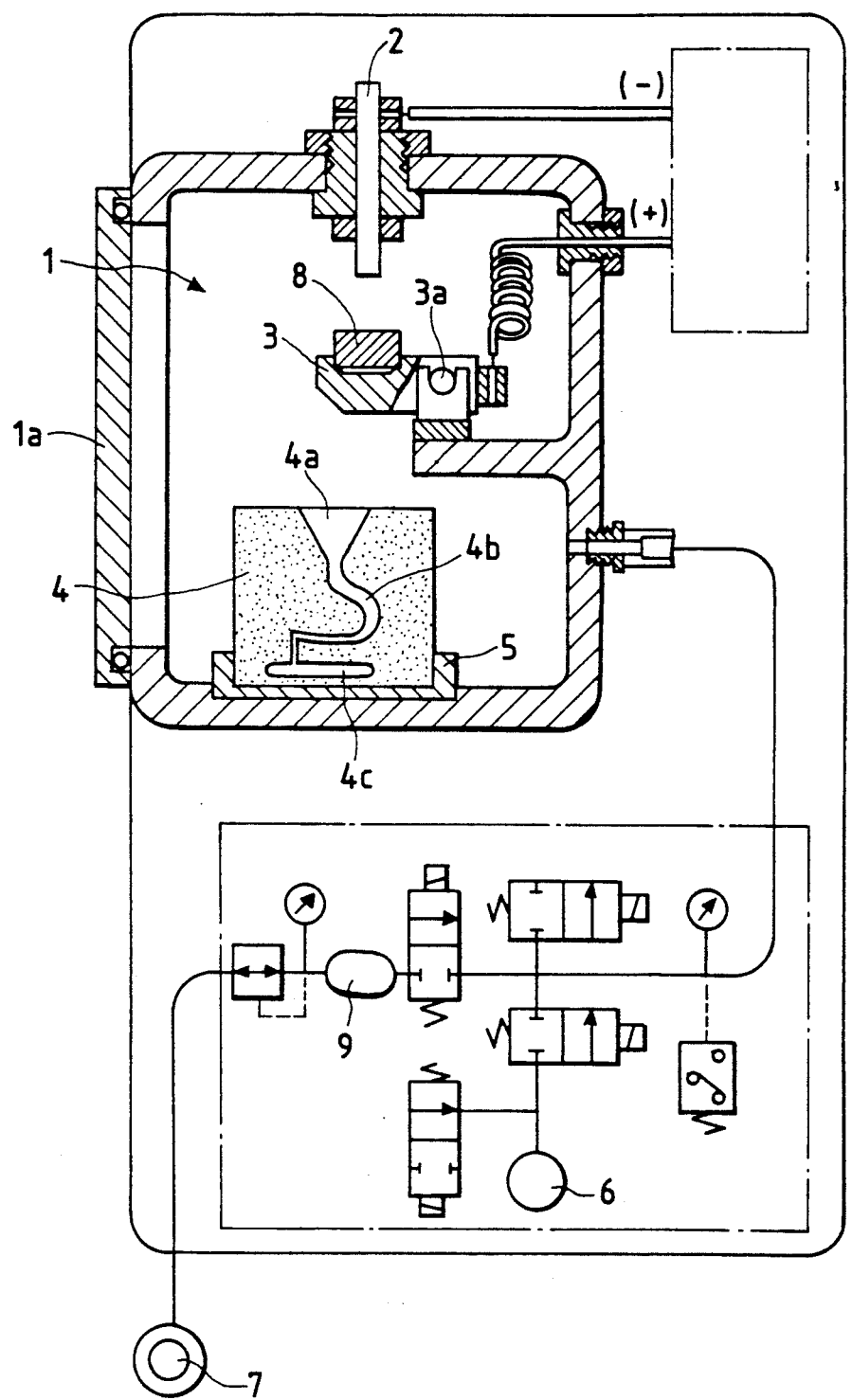
FIG. 1 is a view illustrating part of one embodiment of the casting apparatus for carrying out this invention.

Referring to FIG. 1, there is first provided a casting system including a casting chamber 1 for carrying out the method according to this invention. As illustrated in FIG. 1 this chamber is hermetically sealed with a door 1a closed up, evacuated to vacuum by means of a pump 6, and is filled with an inert gas such as argon fed through an inert gas supply source 7. In the vicinity of the casting chamber 1 and someplace on a pipe for making communication between the gas source 7 and the casting chamber 1, there is preferably located a tank 9, which is designed to receive the inert gas from the gas supply source 7 and feed it into the chamber 1 rapidly. In the casting chamber 1, there are an arc electrode 2 located above and connected to an cathode and a crucible 3 formed of an electrically conductive material, which is located just below the arc electrode 2 and connected to an anode. Below the crucible 3, there is further positioned a mold 4 provided with a closed vent 4c. Preferably, the crucible 3 used is designed to turn up or down pivotally around a horizontal shaft 3a as shown in FIG. 1. However, other types of crucibles, for instance, is one having an openable opening in the bottom (not shown), may be used. The closed vent 4c formed in the mold 4 defines a gas escape passage and communicates with a casting region 4b, in which a molten dental metal hardens, through a small communication hole, having a relatively large volume. As illustrated in FIG. 1, the mold 4 is placed on a dish-form mold support 5 and positioned below the crucible 3.

Figure 2:
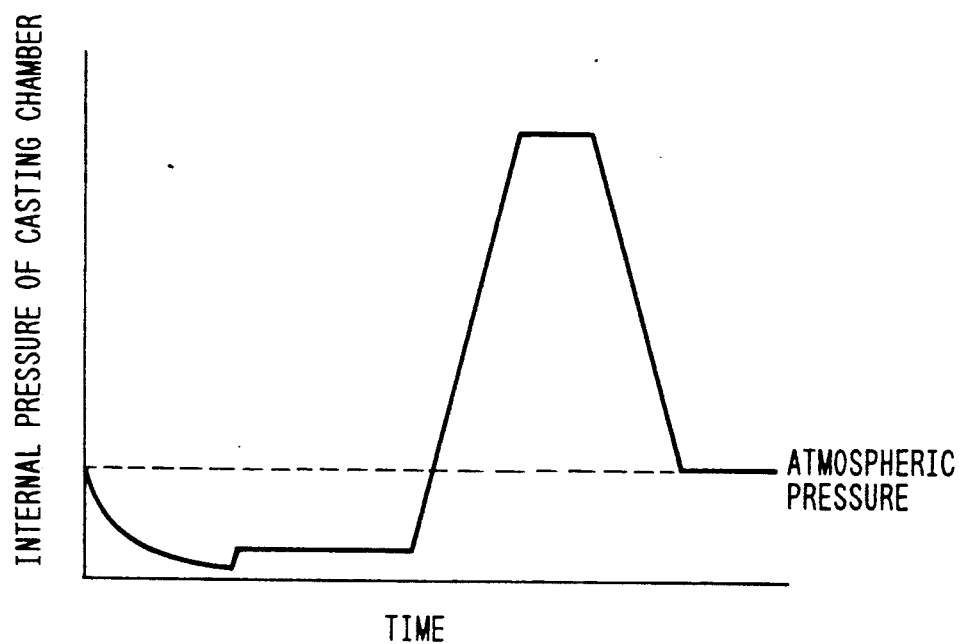
FIG. 2 is a graphical view showing pressure changes in the casting chamber, when the method of this invention is carried out with the casting apparatus of FIG. 1.

Casting of dental metal products with, the casting apparatus may be carried out while controlling the internal pressure in the casting chamber 1 as shown in FIG. 2 by way of example.

First, the mold support 5 with the mold 4 placed on it is located in place within the casting chamber 1. Then, a dental metal ingot 8 is placed on the crucible 3, following by closing the door 1a to keep the casting chamber 1 airtight.

In this state, the casting chamber 1 is evacuated to vacuum by means of the vacuum pump 6. At this time, however, the closed vent 4c is also drawn to substantial vacuum, since it communicates with the casting region 4b and and inlet 4a through the communication hole.

Figure 3A:
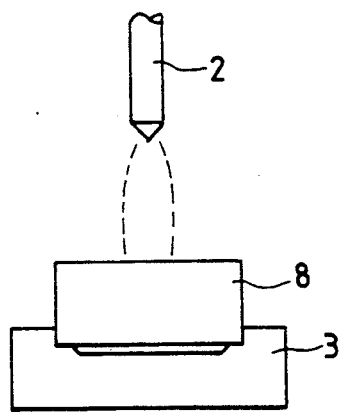
FIG. 3 is views showing states of arc when the pressure in the melting chamber is 3(A) in substantially atmospheric pressure, 3(B) is in a preferred condition, and 3(C) is in state close to vacuum.
Figure 3B:
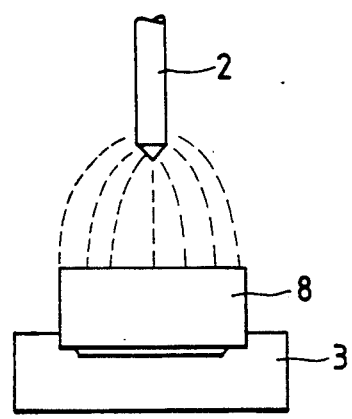
Figure 3C:
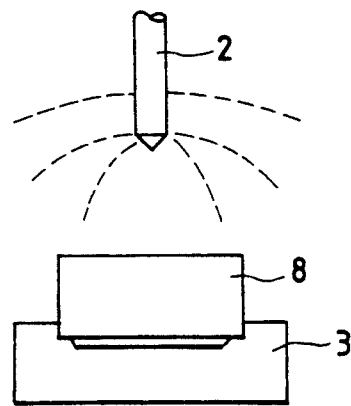

After that, a very small amount of an inert gas such as argon is supplied from the gas source 7 into the casting chamber 1 at such a pressure as to allow arc discharge to be generated all over the upper surface of the ingot 8. Subsequent arc discharge from the arc electrode 2 melts the ingot 8 placed on the crucible 3. In the instant embodiment, the arc electrode 2 used is constructed from tungsten and is 4 mm in diameter, and a titanium ingot 8 in a form of column having a diameter 40 mm and a height of 12 mm is placed on the crucible 3. While the electrode 2 is spaced 7 mm away from the titanium ingot 8, arc discharge is induced all over the upper surface of the ingot 8 at an arc current of 250 A in an argon gas atmosphere of 5 to 150 Torr, as illustrated in FIG. 3(B). However, if the casting chamber 1 is fixed at a pressure nearly equal to atmospheric pressure, as illustrated in FIG. 3(A), then arcs become so fine that they concentrate on the ends of the ingot 8 under the influences of magnetic blow, etc., causing its local melting, and if the casting chamber 1 is kept at a pressure nearly equal to vacuum, as illustrated in FIG. 3(C), then arcs spread so excessively that the ingot 8 is not melted. According to this embodiment, it is possible to melt the dental metal ingot 8 within a short time yet with improved efficiency and establish a delicate pressure condition just before casting.

The thus molten dental metal is poured into the mold 4 through its inlet 4a. If the crucible 3 is designed to turn up or down pivotally around the horizontal shaft 3a, as illustrated in FIG. 1, it is then preferred to pour the molten metal into the mold 4 through its inlet 4a, while electrical current remains conducting between the electrode 2 and the crucible 3. This is because when the crucible 3 turns down, the arc electrode 2 is so spaced away from the molten metal or the other electrode that arc discharge can cease automatically. As a result, the molten metal can be poured into the mold 4 through its inlet 4a immediately following its heating. When the crucible 3 used is designed to have an openable opening in its bottom, arc discharge is stopped after the melting of the metal ingot 8. Immediately after that, the opening is held open to pour the molten metal into the mold 4 through its inlet 4a.

Just after the molten metal has been poured into the mold 4 through its inlet 4a, an additional amount of the inert gas, e.g. argon is supplied from the gas source 7 into the casting chamber 1 to increase its internal pressure, thereby applying pressure to the molten metal from the inlet 4a. Thereupon, gases present in the casting region 4a are forced into the closed vent 4c formed in the mold 4 and having a relatively large volume. However, since the gases in the mold 4 have been at a very low pressure before receiving the molten metal, the degree of a pressure rise in the closed vent 4c is much smaller than the internal pressure in the casting chamber 1, which has been increased by the additional supply of the inert gas from the gas source 7. Thus undisturbed guiding of the molten metal into the casting region 4 is achieved. At this time, the tank 9 having the same volume as that of the casting chamber 1, located in the vicinity of the casting chamber 1 and someplace on the pipe making communication between it and the gas source 7, causes sufficiently rapid pressure rises to occur in the casting chamber, enabling casting to be completed with high casting capabilities.

According to the casting method of this invention which has been explained in greater detail, dental metals can be cast by arc melting occurring at a pressure of an inert gas such as argon gas, so small that arcs spread uniformly all over the upper surfaces of dental metal ingots to melt them simultaneously in their entirety. Thus melting deficiencies due to local arc discharge or disadvantages such as the reaction of dental metals with crucibles are eliminated, while special means for moving electrodes, etc. are dispensed with. Dental metals are unlikely to undergo oxidation, since their casting processes from pouring to hardening occur in an inert gas atmosphere. Rapid and undisturbed pouring of molten dental metal into molds is achieved, even when gases are forced from within the mold into the closed vent as the metals pour into the molds. This is because the in-mold pressure is kept low even at that time. As the molten dental metal are designed to pour into molds at a low in-mold pressure, gases are so forced from within the molds into closed vents that they cannot be entrained in the molten dental metal. If the additional amount of the inert gas is supplied into the casting chamber through a gas tank located in the vicinity thereof, then it is possible to increase the rate of casting, thereby obtaining defect- or cavity-free castings. Thus well-smoothened castings can be obtained using as the investment material a phosphate material having a limited air permeability.

As summarized above, the present method has various advantages of being able to produce dental metal products easily and positively by low-pressure melting and casting without causing casting deficiencies or casting cavities and so makes a great contribution to the dental technical field.

What we claim is:

1. A method for casting dental metals with a casting apparatus including a hermetically sealed casting chamber in which an arc electrode is located above a crucible made of an electrically conductive material, and a mold provided with a closed vent is disposed below said crucible, said method comprising the steps of:
    positioning a dental metal ingot on said crucible,
    evacuating said casting chamber to vacuum,
    feeding a small amount of an inert gas into said casting chamber to produce a pressure of between 5 torr and 150 torr in said casting chamber,
    inducing an arc discharge all over the upper surface of said ingot, thereby melting said ingot placed on said crucible by arc discharge from said arc electrode,
    pouring the thus obtained molten melt into a mold through an inlet, and
    immediately feeding an additional amount of the inert gas into said casting chamber to increase its internal pressure to a level suitable for casting.

2. A method as claimed in claim 1, wherein said additional amount of the inert gas is rapidly fed into said casting chamber through a gas tank located in the vicinity of said casting chamber to increase internal pressure to a level suitable for casting immediately after pouring the thus obtained molten dental metal into said mold through the said inlet.

* * * * *